United States Patent
Baumann et al.

(10) Patent No.: US 7,486,770 B2
(45) Date of Patent: Feb. 3, 2009

(54) FOCUS-DETECTOR ARRANGEMENT OF AN X-RAY APPARATUS FOR GENERATING PROJECTIVE OR TOMOGRAPHIC PHASE CONTRAST RECORDINGS

(75) Inventors: Joachim Baumann, München (DE); Christian David, Lauchringen (DE); Martin Engelhardt, München (DE); Jörg Freudenberger, Eckental (DE); Eckhard Hempel, Fürth (DE); Martin Hoheisel, Erlangen (DE); Thomas Mertelmeier, Erlangen (DE); Franz Pfeiffer, Brugg (CH); Stefan Popescu, Erlangen (DE); Manfred Schuster, München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/700,172

(22) Filed: Jan. 31, 2007

(65) Prior Publication Data
US 2007/0183583 A1 Aug. 9, 2007

(30) Foreign Application Priority Data

| Feb. 1, 2006 | (DE) | ............... 10 2006 004 604 |
| Feb. 1, 2006 | (DE) | ............... 10 2006 004 976 |
| Aug. 9, 2006 | (DE) | ............... 10 2006 037 256 |

(51) Int. Cl.
*G01N 23/04* (2006.01)
(52) U.S. Cl. .............. 378/62; 378/4; 378/21; 378/70; 378/145
(58) Field of Classification Search .......... 378/21, 378/62, 70, 84, 85, 145, 4
See application file for complete search history.

(56) References Cited

U.S. PATENT DOCUMENTS

| 5,812,629 | A | 9/1998 | Clauser | |
| 7,180,979 | B2 * | 2/2007 | Momose | ............... 378/62 |

(Continued)

FOREIGN PATENT DOCUMENTS

DE 10 2006 01290 8/2007

(Continued)

OTHER PUBLICATIONS

Weitkamp et al., "X-ray phase imaging with a grating interferometer", Optics Express 2005, vol. 12, No. 16, pp. 6296-6304.

(Continued)

*Primary Examiner*—Jurie Yun
(74) *Attorney, Agent, or Firm*—Harness, Dickey & Pierce PLC (57) ABSTRACT

A focus-detector arrangement includes a radiation source with a focus, arranged on a first side of the subject, for generating a fan-shaped or conical beam of rays; at least one X-ray optical grating arranged in the beam path, with at least one phase grating arranged on the opposite second side of the subject in the beam path generating an interference pattern of the X-radiation preferably, in a particular energy range; and an analysis-detector system which detects at least the interference pattern generated by the phase grating in respect of its phase shift with position resolution. According to at least one embodiment of the invention, at least one X-ray optical grating including bars which are free from overhangs form shadows in the beam path of the fan-shaped or conical beam of rays.

53 Claims, 4 Drawing Sheets

U.S. PATENT DOCUMENTS

| | | |
|---|---|---|
| 2001/0001010 A1 | 5/2001 | Wilkins |
| 2005/0207012 A1 | 9/2005 | Arnold et al. |
| 2005/0286680 A1 | 12/2005 | Momose |
| 2007/0189449 A1 | 8/2007 | Baumann et al. |

FOREIGN PATENT DOCUMENTS

| | | |
|---|---|---|
| DE | 10 2006 015355 | 8/2007 |
| DE | 10 2006 015356 | 8/2007 |
| DE | 10 2006 015358 | 8/2007 |
| DE | 10 2006 017291 | 8/2007 |
| EP | 1 447 046 A1 | 8/2004 |

OTHER PUBLICATIONS

D. Vaughan (ed.), "X-Ray Data Booklet", Lawrence Berkeley Laboratory, Berkley, 1986, pp. 2-28, 2-29.
U. Bonse and M. Hart, "An X-ray Interferometer", Appl. Phys. Lett., 1965, vol. 6, No. 8, pp. 155-156.
Ingal and Beliaevskaya, "X-ray plane-wave topography observation of the phase contrast from a non-crystalline object", J. Phys. D: Appl. Phys. 28, 1995, pp. 2314-2317.
R. Fitzgerald, "Phase-Sensitive X-Ray Interferometer", Physics Today, 53, 2000, pp. 23-26.
Chapman et al., "Diffraction enhanced x-ray imaging", Phys. Med. Biol. 42, 1997, pp. 2015-2025.
Wilkins et a., "Phase-contrast imaging using polychromatic hard X-rays", Nature 384, 1996, pp. 335-338.
V. Lehmann, The Physics of Macropore Formation in low Doped n-Type Silicon, J. Electrochemical Soc. 140 (10), 1993, pp. 2836-2843.
Bergmann, Schäfer, "Lehrbuch der Experimentalphysik", vol. 1, Mechanik, Akustik, Wärme, De Gruyter, Berlin, 1970, pp. 542-554.
Shack et al., J. Opt. Soc. Am. 61, 1971, p. 656.
Platt et al., "History and Principles of Shack-Hartmann Wavefront Sensing", Journal of Refractive Surgery, vol. 17, 2001, pp. 573-577.
F. Roddier, "Variations on a Hartmann theme", Opt. Eng. 29, 1990, pp. 1239-1242.
Primot et al., "Deconvolution from wave-front sensing: a new technique for compensating turbulence-degraded images", J. Opt. Soc. Am. 7(9), 1990, pp. 1598-1608.
J.C. Wyant, "White Light Extended Source Shearing Interferometer", Appl. Opt. 13, 1974, pp. 200-202.
C. L. Koliopoulos, "Radial grating lateral shear heterodyne interferometer", Appl. Opt. 19, 1980, pp. 1523-1528.
J. Primot, L. Songo, "Achromatic three-wave (or more) lateral shearing interferometer", J. Opt. Soc. Am. A, 12(12), 1995, pp. 2679-2685.
J. Primot, "Theoretical description of Shack-Hartmann wave-front sensor", Optics Communications, 222, 2003, pp. 81-92.
V. Ronchi, "Forty Years of History of a Grating Interferometer", Appl. Opt. 3(4), 1964, pp. 437-451.
Schroer et al., "Hard x-ray nanoprobe based on refractive x-ray lenses", Appl. Phys. Lett. 87, 124103, 2005.
M. Bavdaz, N. Gurker, "Coded Imaging X-ray Microprobe", X-Ray Spectrometry, 22, 1993, pp. 65-70.
Momose et al. "Tomographic image reconstruction using X-ray phase information", SPIE, vol. 2708, pp. 674-684.
Barty et al., "Time-gated medical imaging with ultrafast laser plasma x-rays", SPIE, vol. 2523, pp. 286-298.
C. J. Kotre, I. P. Birch, "Phase contrast enhancement of x-ray mammography: a design study", Phys. Med. Biol., 44, 1999, pp. 2853-2866.
Arfelli et al, "Low-dose phase contrast x-ray medical imaging", Phys. Med. Biol. 43, 1998, pp. 2845-2852.
Herrlin et al., "Contrast-Enhanced Radiography by Differential Absorption Using a Laser-Produced X-Ray Source", Investigative Radiology 32, 1997, pp. 306-310.
Grätz et al., "Time-Gated Imaging in Radiology: Theoretical and Experimental Studies", IEEE J. of selected Topics in Quantum Electronics, 2(4), 1996, pp. 1041-1048.
Murnane et al., "Ultrafast X-ray Pulses from Laser-Produced Plasmas", Science, vol. 251, 1991, pp. 531-536.
Krol et al., "Laser-based microfocused x-ray source for mammography: Feasibiliy study", Med. Phys. 24(5), 1997, pp. 725-732.
Piestrup et al., "A design of mammography units using a quasiminichromatic x-ray source", Review of Scientific Instruments, 72(4), 2001, pp. 2159-2170.
C. G. Schroer, B. Lengler, "Focusing Hard X Rays to Nanometer Dimensions by Adiabatically Focusing Lenses", Phys. Rev. Lett. 94, 054802, 2005.
Heilman et al.; Reflection Grating Development Update, Constellation-X Facility Science Team Meeting, Nov. 19-20, 2003.
Office Action for corresponding German Application No. 10 2006 037 256.5-52 dated Aug. 9, 2007.

* cited by examiner

FOCUS-DETECTOR ARRANGEMENT OF AN X-RAY APPARATUS FOR GENERATING PROJECTIVE OR TOMOGRAPHIC PHASE CONTRAST RECORDINGS

PRIORITY STATEMENT

The present application hereby claims priority under 35 U.S.C. §119 on German patent application numbers DE 10 2006 004 976.4 filed Feb. 1, 2006, DE 10 2006 004 604.8 filed Feb. 1, 2006, and DE 10 2006 037 256.5 filed Aug. 9, 2006, the entire contents of each of which is hereby incorporated herein by reference.

FIELD

Embodiments of the invention generally relate to a focus-detector arrangement of an X-ray apparatus for generating projective or tomographic phase contrast recordings of a subject. For example, they may relate to one including a radiation source with a focus, arranged on a first side of the subject, for generating a fan-shaped or conical beam of rays, a phase grating arranged on the opposite second side of the subject in the beam path, which generates an interference pattern of the X-radiation preferably in a particular energy range, and an analysis-detector system which detects at least the interference pattern generated by the phase grating in respect of its phase shift with position resolution.

BACKGROUND

Focus-detector arrangements for generating projective or tomographic phase contrast recordings of a subject are widely known. For example, reference is made to the European patent application EP 1 447 046 A1 and the German patent applications (not yet published at the priority date of the present application) with the file references 10 2006 017 290.6, 10 2006 015 358.8, 10 2006 017 291.4, 10 2006 015 356.1 and 10 2006 015 355.3.

For imaging by ionizing rays, in particular X-rays, principally two effects can be observed which occur when the radiation passes through matter, namely absorption and the phase shift of the radiation passing through a subject. It is known that in many cases, the phase shift when a ray passes through a subject depends much more strongly on small differences with respect to the thickness and composition of the penetrated matter than the absorption does. In principle, the magnitudes of the two effects respectively depend on the energy of the radiation and the atomic number of the penetrated matter.

For such phase contrast radiography or phase contrast tomography, the phase shift of radiation due to the object is evaluated. Here, similarly as X-radiography or X-ray tomography, both projective images of the phase shift or even a multiplicity of projective images of tomographic representations of the phase shift can be calculated.

The phase of an X-ray wave cannot be determined directly, rather only by interference with a reference wave. The phase shifts relative to reference waves or neighboring rays can be measured by using interferometric gratings and compiled for projective and tomographic recordings. In respect of these interferometric measurement methods, reference is made to the documents cited above. In these methods, coherent X-radiation is passed through a subject, then delivered through a grating with a period adapted to the wavelengths of the radiation so as to create an interference pattern, which depends on the phase shift occurring in the object. This interference is measured by a downstream (subsequent=chronological) analysis-detector arrangement, so that the phase shift can be determined with position resolution. It is also known to produce such phase gratings for example by etching rectangular structures on a silicon wafer.

Previous systems for differential phase contrast radiography/tomography are configured for the parallel ray geometry. It has been found that the imaging in such systems functions satisfactorily only in the near-axial region, and becomes worse with an increasing fan and cone angle toward the edge of the detector.

For medical diagnosis and nondestructive material testing, a more compact structure of the X-ray system used is desirable. In computer tomography (CT) for example the source, the phase contrast grating system and the detector must rotate in a portal whose diameter is limited for system reasons and owing to the centrifugal force. The aperture of medical CT systems is furthermore dictated by the dimensions of the patient and the required ergonomics. These dimensions establish a maximal length for the beam path of the differential phase contrast imaging system. On the other hand, the field of view should be large enough to achieve a meaningful scan. This makes it necessary to use a wide fan or cone beam. Similar situations and considerations also apply to X-ray systems for projective recordings or C-arc systems.

SUMMARY

In at least one embodiment of the invention, a focus-detector arrangement is provided which has improved imaging in the entire off-axial region or edge region of the detector system.

The Inventors have discovered, in at least one embodiment, that one reason for the inferior imaging in phase contrast recording toward the edge of the detector is at least partly that the alignment of the grating bars in the edge region of conventional plane gratings assumes a greater and greater angle with an increasing distance from the center. Owing to the relatively high photon energies of usually >20 keV, aspect ratios of bar height to gap width in the range of more than 10:1 are encountered in the grating, and specifically both in the phase grating and in the analyzer grating. The bar height of the phase gratings increases approximately linearly with the photon energy, and the bar height of the analyzer grating even more strongly, which leads to enormous aspect ratios at the high photon energies of medical diagnosis and nondestructive material testing. When beam paths with broader fan or cone angles are intended to be used, these gratings with a large aspect ratio cause a shadowing effect which greatly impairs in particular the diffraction effect of the phase grating and the scan effect of the analyzer grating at larger angles, i.e. toward the edge of the detector.

If such negative effects are intended to be avoided, then it is necessary to have a corresponding configuration of the gratings which avoids shadowing or overhang relative to the beam direction of incident rays.

Such shadowing may, for example, be avoided by designing the grating bars so that their flanks are oriented in the respective ray direction. It is also possible to design the bars trapezoidally so that shadowing does not occur at any position of the grating. Correspondingly, a corrugated contour which avoids shadowing may also be selected. A grating may particularly advantageously also have a corrugated profile of the bars, which prevents shadowing with a flank profile which is not too steep.

A conventional grating with perpendicular flanks may furthermore be used, if it is curved circularly around the source point of the radiation. In this case, the grating bars which are therefore aligned radially extend perpendicularly to the sphere surface or circular cylinder surface spanned in this way.

Such curvature of the grating may for example be generated by appropriate clamping, or by using a flexible grating as an interface between two cells at different atmospheric or hydraulic pressure, supports being applied peripherally. In fan or cone beam geometry, the differential phase contrast method requires not only a phase grating in the form of a cylinder section or a spherical cap but also, owing to the formation of concentric interference patterns, a concentric analyzer grating and possibly also concentric detectors in the form of cylinder sections or spherical caps. This constitutes a technical difficulty. To this end the Inventors furthermore propose that, in at least one embodiment, individually or in combination, the bar height or the grating period of the phase grating be adapted according to the geometrical proportions so that the respective radial distance of the phase grating from the analyzer-detector arrangement corresponds to the desired Talbot distance.

The following should also essentially be pointed out:

The emission of X-ray photons from laboratory X-ray sources (X-ray tubes, secondary targets, plasma sources, radioactive sources) as well as by conventional synchrotron radiation sources of the first to third generations is subject to stochastic processes. The emitted X-radiation therefore has no spatial coherence per se. In phase contrast radiography and tomography or any interference experiment, however, the radiation of X-ray sources behaves as coherent radiation when the observation angle at which the source appears to the observer or the object, the grating or the detector, is sufficiently small. The so-called spatial coherence length $L_c$ can be provided as a measure of the spatial or transverse coherence of an extended X-ray source:

$$L_c = \lambda \frac{a}{s}.$$

Here, $\lambda$ is the wavelength, s is the transverse source size and a is the source-observation point distance. Many authors also refer to half the above-defined value as the spatial coherence length. The exact value is incidental; what is important is that the coherence length $L_c$ is large compared to the (transverse) dimension of the spatial region from which rays are intended to interfere with one another.

In the context of the patent application, the term coherent radiation is intended to mean radiation which leads to the formation of an interference pattern under given geometries and given distances of the X-ray optical gratings. It is self-evident that the spatial coherence and therefore the spatial coherence length is always determined by the trio of quantities: wavelength, source size and observation distance. With a view to compact formulation, this fact has been abbreviated to terms such as "coherent X-radiation", "coherent X-radiation source" or "point source for generating coherent X-radiation". The basis for these abbreviations is that the wavelength (or the energy E) of the X-radiation in the applications discussed here is limited by the desired penetrability of the subject on the one hand and the spectrum available in laboratory X-ray sources on the other hand. The distance a between the source and the observation point is also subject to certain restrictions in laboratory equipment for nondestructive material testing or medical diagnosis. This usually leaves only the source size s as a single degree of freedom, even though the relationships between source size and tube power set narrow limits here.

The requirement for a small or point-like radiation source means that the available intensity is also relatively low. In order to increase the intensity, it has therefore also been proposed to use an X-ray source with a relatively large-area focus and to place an X-ray optical absorption grating, a so-called source grating, in the beam path between the focus and the subject. The large-area focus makes it possible to use larger and therefore more powerful X-ray sources. The narrow slits or gaps of the source grating ensure that all the rays, which have to emerge from the same slit, comply with the requisite spatial coherence. The slit width must satisfy the size requirement given by Equation (1) for the transverse source size s. Correct superposition, at least in terms of intensity, of the maxima and minima of the standing wave field is possible between the photons from slit to slit of the source grating with suitable tuning of the source grating period $g_0$ and the interference pattern period $g_2$ as well as the distance l between the source grating $G_0$ and the phase grating $G_1$ and the distance d between the phase grating $G_1$ and the interference pattern according to $$g_0/g_2 = l/d \tag{2}$$

In the abbreviated formulation of the patent application, the term "quasi-coherent radiation" or "quasi-coherent radiation source" is used in this context.

The temporal or longitudinal coherence of the radiation is associated with the monochromaticity of the X-radiation or of the X-radiation source. The X-radiation of intense characteristic lines usually has a sufficient monochromaticity or temporal coherence length for the applications discussed here. Upstream monochromators or selection of the resonant energy via the bar height of the phase grating can also filter out a sufficiently narrow spectral range from a Bremsstrahlung spectrum or synchrotron spectrum, and thus satisfy the requirements for the temporal coherence length in the present arrangements.

According to these basic concepts, the Inventors propose, in at least one embodiment, to improve a focus-detector arrangement for an X-ray apparatus, which is used to generate projective or tomographic phase contrast recordings of a subject and consists at least of:

a radiation source with a focus, arranged on a first side of the subject, for generating a fan-shaped or conical beam of rays, at least one X-ray optical grating arranged in the beam path, with at least one phase grating arranged on the opposite second side of the subject in the beam path generating an interference pattern of the X-radiation, preferably in a particular energy range, and an analysis-detector system which detects at least the interference pattern generated by the phase grating in respect of its phase shift with position resolution.

The inventive improvement, in at least one embodiment, resides in that at least one X-ray optical grating includes bars which are free from overhangs forming shadows in the beam path of the fan-shaped or conical beam of rays. At each position in the beam direction, such gratings thus include bars and gaps so that the transition region between the bars and gaps takes place abruptly in the direction of the respective current ray, such that the transition edges extend parallel to the beam direction.

Such an embodiment can be achieved, for example, in that an X-ray optical grating is designed to be curved around the focus at least in a first section plane, in which case the at least one X-ray optical grating may preferably have a constant radius of curvature around the focus in the first section plane.

The X-ray optical grating may additionally be designed to be curved around the focus in a second section plane perpendicular to the first. The effect achieved by this is that every position of the X-ray optical grating has the same distance around the focus, i.e. it extends over a sphere surface around the focus.

According to a particular design of at least one embodiment of the invention, the bars of the at least one X-ray optical grating may exclusively include rising and falling flanks which are aligned radially toward the focus.

Such curvature of the grating may for example be generated by appropriate clamping, or by using a flexible grating as an interface between two cells at different atmospheric or hydraulic pressure, supports being applied peripherally.

According to one example embodiment of the focus-detector arrangement, in particular the phase grating, the curvature of the phase grating in a plane is induced by clamping between at least three, preferably four support elements. In this case, at least one of the support elements may bear pointwise or linearly on the phase grating. If these support elements are arranged mutually offset, then a different curvature in one or more planes can be achieved depending on the pressure exerted on the support elements and depending on the flexibility of the grating. In this way, a grating originally manufactured to be flat can be curved in the desired way. In principle it is also feasible for gravitational forces and centrifugal forces possibly occurring, such as may occur in CT systems, to be compensated for variably by adapting the pressure on the support elements.

According to another alternative embodiment, the X-ray optical grating constitutes a bounding surface between at least two regions of different gas pressure and the desired curvature of the grating in at least one plane is at least additionally induced by the pressure difference between the regions of different gas pressure. Here again, the curvature may be influenced by varying the pressure. It should furthermore be pointed out that instead of gas, at least on one side of the grating it is also possible to use a liquid.

In a fundamentally different embodiment, a flat X-ray optical grating is proposed instead of curving the entire grating, the grating bars being designed here according to the basic concept of the invention so that no shadowing occurs. This may, for example, be done by appropriate alignment of configuration or the grating bars.

It should, however, be pointed out that it is also within the scope of at least one embodiment of the invention to use a combination of a grating curved two-dimensionally on the surface and a flat grating with bars aligned in the beam direction.

According to at least one embodiment of the invention, the bars of the grating are aligned radially toward the focus in at least one section plane, and optionally in two mutually perpendicular section planes.

It is furthermore proposed that the bars of an X-ray optical grating should have an at least substantially sinusoidal height profile in at least one or the first section plane along the beam path.

On the other hand, the bars of the phase grating may also have a sinusoidal or curvilinear or trapezoidal height profile in two mutually perpendicular section planes along the beam path. This embodiment is advantageous particularly when using ray bundles whose fanning is pronounced in two planes.

According to a development of an embodiment of the inventive concept for adapting the curvature of the grating surface and for concomitantly influencing the Talbot distance of the phase grating and possibly adapting to given geometrical proportions in the focus-detector arrangement, the Inventors furthermore propose that there should be a different distance from the phase grating to the analysis-detector system over the extent of the phase grating.

In this case, the bars of the phase grating may be given different bar lengths in order to adapt the Talbot distance to a different distance from the analysis-detector system. The bars of the phase grating may also include different grating periods in order to adapt the Talbot distance to a different distance from the analysis-detector system. A combination of the latter two features is likewise possible.

As an alternative to the variant presented above, an equidistant focus-detector arrangement is proposed in which the distance to the analysis-detector system remains the same over the extent of the phase grating.

Here, in one embodiment, the bars of the phase grating may comprise the same bar lengths with a different bar height in order to adapt the Talbot distance to the same distance from the analysis-detector system. For clarification, it should be mentioned that the bar heights and the bar lengths are the same in the case of perpendicular bars.

According to another embodiment, the bars of the phase grating may include different grating periods with the same bar height and different bar length in order to adapt the Talbot distance to the same distance from the analysis-detector system. Combinations of the latter features are also possible.

It is furthermore proposed that the following geometrical condition be satisfied at least for the average value of the radial distances from the focus to the phase grating and from the focus to the analysis-detector system:

$$g_2 = \frac{1}{2} \cdot \frac{r_2}{r_1} \cdot g_1,$$

where:
$r_1$=radial distance from the focus to the phase grating;
$r_2$=radial distance from the focus to the analysis-detector system;
$g_1$=period of the phase grating $G_1$;
$g_2$=period of the analyzer grating $G_2$ in the analysis-detector system.

The inventors also propose that the following geometrical condition be satisfied in a focus-detector arrangement for phase contrast measurement with fanned ray bundles:

$$r_1 > \frac{g_1^2}{2\lambda},$$

where:
$r_1$=radial distance from the focus to the phase grating;
$g_1$=period of the phase grating ($G_1$);
$\lambda$=wavelength of the energy of the X-radiation in question.

The following geometrical condition should furthermore be satisfied:

$$r_2 - r_1 = d_m = \left(m - \frac{1}{2}\right) \cdot \frac{g_1^2}{4 \cdot \lambda},$$

where:
r₁=radial distance from the focus to the phase grating;
r₂=radial distance from the focus to the analysis-detector system;
g₁=period of the phase grating (G₁);
$d_m$=distance from phase grating to analysis-detector system, corresponding to the $m^{th}$ order Talbot distance;
λ=wavelength of the energy of the X-radiation in question.

The following geometrical condition should furthermore be satisfied:

$$2\Theta > \Delta\alpha/2,$$

where:
Θ=half the first order diffraction angle of the X-radiation in question on the phase grating with $\Theta = \arcsin(\lambda/2g_1)$;
Δα=cone angle of the phase grating according to $\Delta\alpha = \operatorname{arc}(g_1/r_1)$;
g₁=period of the phase grating (G₁);
r₁=radial distance from the focus to the phase grating;
λ=wavelength of the energy of the X-radiation in question.

The focus-detector arrangement described above may in principle be equipped with a focus which is substantially designed to be point-like. An advantage in this case is that there are very well defined geometrical proportions. With very small focus dimensions, however, the maximal dosage is usually insufficient to carry out CT examinations with such a system, since the scan times become too long.

In order to achieve high dosages in this case, it is proposed to equip the focus-detector arrangement for example with a focus designed to be flat and an additional source grating for generating a beam of individually coherent rays, arranged between the focus and the subject. It should nevertheless be pointed out that focus configurations (for example multi-strip focus) which generate a beam of quasi-coherent rays without a source grating, are also regarded as equivalent without departing from the scope of the invention.

The scope of embodiments of the invention also covers a focus-detector arrangement in which the analysis-detector system is designed as a combination of a position-resolving detector and an analysis grating upstream in the radiation direction for determining the average phase shift of the X-radiation of a particular energy per detector element. Here again, the detector of the analysis-detector system may have a curvature around the focus and/or the analyzer grating of the analysis-detector system may have a curvature around the focus.

The analysis-detector system may furthermore be designed as a position-resolving detector, the detector elements including an internal structure which is suitable for determining the average phase shift of the X-radiation per detector element. In this variant as well, the detector of the analysis-detector system may have a curvature around the focus, preferably with a constant radius.

In another proposed embodiment of the focus-detector arrangement according to the invention, the distance from the focus to the subject may be designed so that it is small (½x-1/10x) to very small (<1/10x) relative to the distance from the subject to the analysis-detector system. This achieves a corresponding magnification effect.

The inventive principle of embodiments of the invention may, for example, be used in an X-ray system for generating projective phase contrast recordings, an X-ray C-arc system for generating projective or tomographic phase contrast recordings, or an X-ray CT system for generating tomographic phase contrast recordings.

BRIEF DESCRIPTION OF THE DRAWINGS

The invention will be explained in more detail below with reference to example embodiments with the aid of the figures, only the features necessary for understanding the invention being represented. Here, the following references are used: 1: computer tomography system; 2: first X-ray tube; 3: first detector; 4: second X-ray tube; 5: second detector; 6: gantry housing; 7: patient; 8: patient support; 9: system axis; 10: control and computation unit; 11: memory; 12: axis; 13: interference pattern; 14: bars; 15: gaps; 16: support element; 17: seal; 18: supporting forces; 19: window; 20.1, 20.2: chamber halves; $D_1$: detector; d: distance; $d_m$: Talbot distance; E: energy; $E_x$: detector elements; $F_1$: focus; $G_0$: source grating; $G_1$: phase grating; $G_2$: analyzer grating; $g_0, g_1, g_2$: period of the grating lines; $h_0, h_1, h_2$: height of the grating bars; I: intensity; l: distance; n: refractive index; P: sample; $\operatorname{Prg}_n$: program; $r_1$: radial distance from the focus to the phase grating; $r_2$: radial distance from the focus to the analysis-detector system; $S_i$: X-ray; x, y, z: cartesian coordinates; $X_G$: offset of the analysis grating; Θ: half the first order diffraction angle of the X-radiation in question on the phase grating with $\Theta = \arcsin(\lambda/2g_1)$; Δα: cone angle of the phase grating period according to $\Delta\alpha = \operatorname{arc}(g_1/r_1)$; λ: wavelength of the energy of the X-radiation in question; $\phi_{ij}$: relative phase shift between the detector elements; $\phi_x$: phase shift at the detector element $E_x$.

In detail.

DETAILED DESCRIPTION OF THE EXAMPLE EMBODIMENTS

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

For better understanding, the basic principle of phase contrast measurement will be described below with FIGS. 1 to 3. In this regard it should essentially be noted that the figures are not shown true to scale, rather they are intended to highlight the basic structure and the described effects. The transverse axis is expanded relative to the longitudinal axis (=optical axis). The angles are therefore represented with an exaggerated size. For didactic reasons, the interference pattern and the analyzer grating in particular have been shown somewhat spatially separated from one another, even though it is precisely the object of the method to position the analyzer grating at the maximum of the interference pattern, i.e. at the $1^{st}$ Talbot distance. The dimensions d and $r_2$ therefore refer both to the interference pattern and to the analyzer grating.

Figure 1:
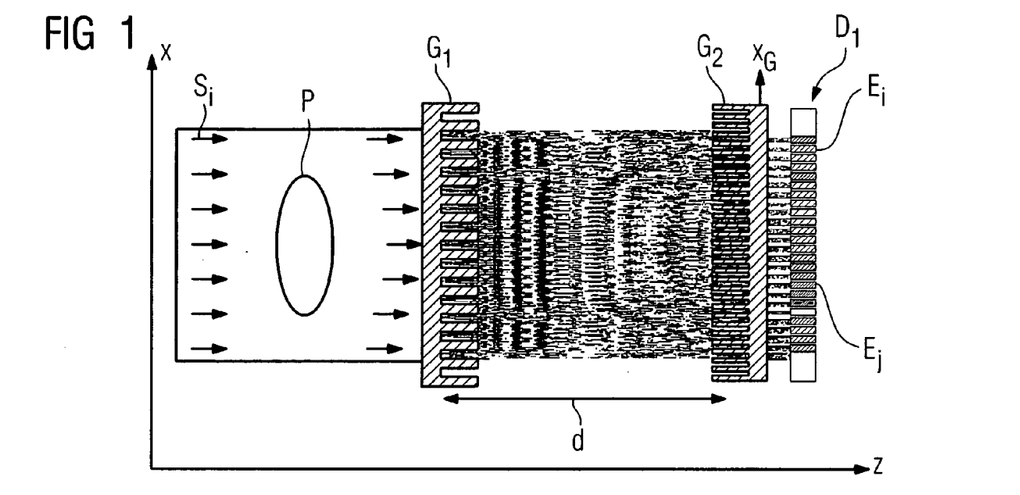
FIG. 1: shows a longitudinal section through an outline representation of a focus-detector arrangement with a phase grating, an analyzer grating and a detector for representing the interference phenomenon.

FIG. 1 shows coherent radiation coming from a point-like radiation source or quasi-coherent radiation crossing a source grating, which passes through a sample P, a phase shift taking place when passing through the sample P. When passing through the grating $G_1$ an interference pattern is generated, as represented by the gray shading, which with the aid of the grating $G_2$ leads to different radiation intensities per detector element on the downstream detector $D_1$ and its detector elements, an interference pattern being formed at a so-called Talbot distance.

Figure 2:
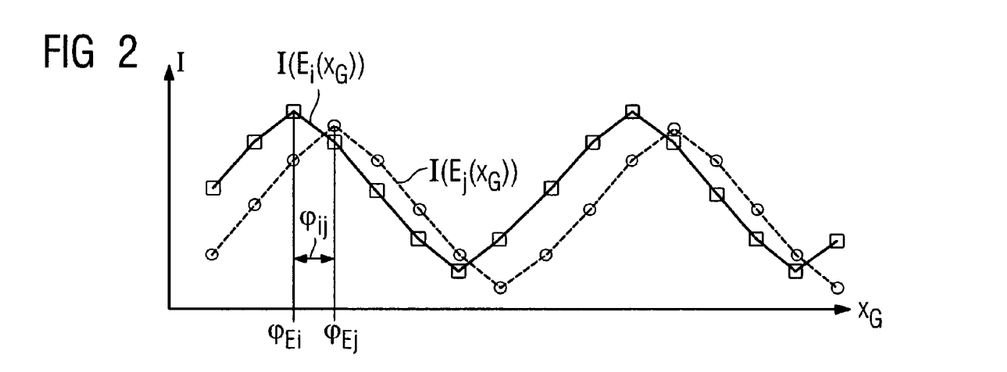
FIG. 2: shows the intensity profile on selected detector elements as a function of the relative position of the analyzer grating from the interference pattern.

If the detector element $E_i$ for example is considered as a function of the relative position $x_G$ of the analyzer grating $G_2$ and the intensity $I(E_i(x_G))$ is plotted as a function of the relative position $x_G$ against the intensity, then a sinusoidal profile of the intensity I at this detector element $E_i$ is obtained as shown in FIG. 2. If this measured radiation intensity I is plotted for each detector element $E_i$ or $E_j$ as a function of the offset $x_G$, then the function $I(E_i(x_G))$ or $I(E_j(x_G))$ can be approximated for the various detector elements, which in the end form the geometrical X-ray between the focus and the respective detector element. The phase shift $\phi$ and the relative phase shift $\phi_{ij}$ between the detector elements can be determined for each detector element from the functions.

For each ray in space, the phase shift per ray can therefore be determined by at least three measurements with a respectively offset analyzer grating, from which either the pixel values of a projective recording can be calculated directly in the case of projective X-ray recordings, or projections whose pixel values correspond to the phase shift can be compiled in the case of a CT examination, so that with the aid of reconstruction methods known per se it is possible to calculate therefrom which volume element in the subject is to be ascribed to which component of the measured phase shift. Section images or volume data are thus calculated therefrom, which reflect the effect of the examined object in respect of the phase shift of X-radiation with position resolution. Since even minor differences exert a strong effect on the phase shift in this context, very detailed and high-contrast volume data can be obtained from materials which are relatively similar per se, in particular soft tissue.

This variant of detecting phase shifts of the X-rays which pass through a subject, with the aid of a multiply offset analyzer grating and measuring the radiation intensity on a detector element behind the analyzer grating, means that at least three measurements of each X-ray have to be carried out with an analyzer grating respectively displaced by fractions of the grating period.

In principle, it is even possible to make do without such an analyzer grating and use a sufficiently fine-structured detector instead, in which case the dose losses due to absorption in the bars of the analyzer grating are obviated and the phase shift in the relevant ray can be determined by a single measurement.

In order to measure the phase contrast, it is necessary to use coherent radiation. This may be generated for example by a point-like focus or as a field of quasi-coherent radiation by a source grating behind a focus, which is designed to be flat, or by a corresponding grating-like configuration of the focal spot on the anode in order to replicate such a grating.

Figure 3:
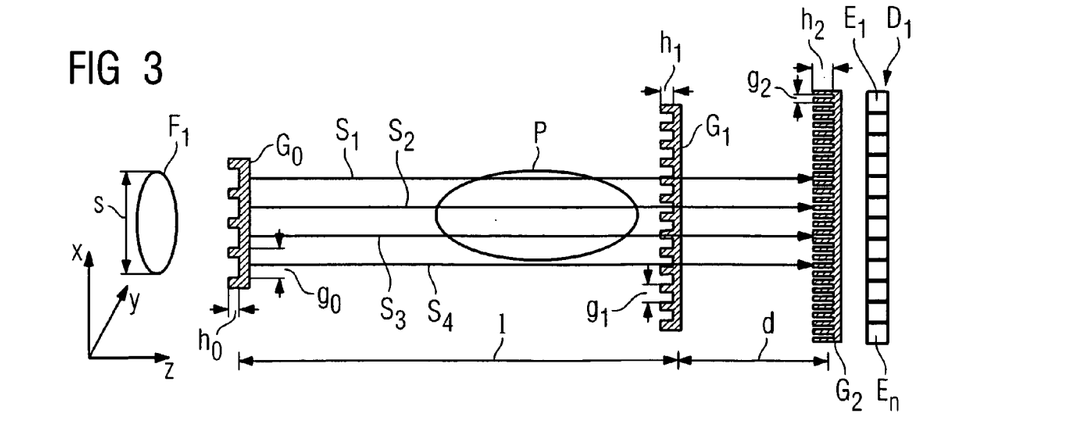
FIG. 3: shows a longitudinal section through a focus-detector system with the arrangement of the source grating, the phase grating and the analyzer grating.

Such a variant of a focus-detector system, in which a field of quasi-coherent radiation is generated by a source grating behind a focus $F_1$, which is designed to be flat, is schematically shown in FIG. 3. Owing to the high available dosage, such an embodiment is also suitable for CT systems. In principle all gratings $G_0$, $G_1$ and $G_2$ represented there may be replaced by shadow-free or low-shadow gratings according to an embodiment of the invention.

The focus $F_1$, the greatest extent of which is denoted by s, lies in front of the first grating $G_0$. The quasi-coherent X-rays which come from the source grating $G_0$ are denoted by $S_1$ to $S_4$. This first grating $G_0$ has a grating line period $g_0$ and a grating bar height $h_0$. Correspondingly, the gratings $G_1$ and $G_2$ are also provided with a height $h_1$ and $h_2$, respectively and a period $g_1$ and $g_2$, respectively. In order for the phase measurement to function, it is necessary that the distance l between the grating $G_0$ and the grating $G_1$ and the linear distance d between the grating $G_1$ and the grating $G_2$ should be in a particular mutual ratio. Here:

$$g_0 = g_2 \frac{l}{d}.$$

The distance of the detector $D_1$ with its detector elements $E_1$ to $E_n$ from the analyzer grating $G_2$ is of secondary importance. The height $h_1$ of the bars of the phase grating should be selected so that the following formula is satisfied according to the wavelengths in question, i.e. the relevant energy of the X-radiation, and in relation to the respective grating material:

$$h_1 = \frac{\lambda}{2(n-1)}$$

Here, n denotes the refractive index of the grating material and $\lambda$ denotes the wavelengths of the X-radiation, at which the phase shift is intended to be measured. It should also be noted that the equations mentioned above apply strictly speaking only for the parallel beam geometry, and need to be adapted accordingly when a fan beam geometry is used.

The height $h_2$ of the analysis grating must be sufficient in order to generate effective absorption differences between the bars through which the X-radiation passes and the substantially free positions of the grating, in order to register the intensity distribution of the interference pattern with position resolution and intensity/gray value resolution and make it compatible with the further data processing.

The line orientation of the gratings $G_0$ to $G_2$ will generally be selected so that the grating lines of the gratings provided, and possibly provided strip structures of the detector elements, extend mutually parallel. It is furthermore advantageous, but not necessary, that the grating lines should be oriented parallel or perpendicularly to the system axis of the rotating focus-detector system presented here.

Considering in more detail the representation of the gratings and the fan-shaped designed radiation or the fan-shaped ray beam in FIG. 3, it can be seen that an obliquely extending ray $S_i$ at the edges of the grating bars leads to shadowing. In reality, however, the grating bars are designed to be substantially higher relative to the bar spacing or the grating period, i.e. the aspect ratio is larger, so that this shadowing effect actually occurs much more significantly with even minor deviations from the optical axis. Furthermore, the fanning of the beam is sometimes much greater than as schematically represented in FIG. 3. The consequence of this is that the principle of phase contrast measurement scarcely still functions with large fan or cone angles and large aspect ratios at high X-ray energies in the edge regions of flat conventional gratings, because of the shadowing effects which occur ever more greatly.

Figure 4:
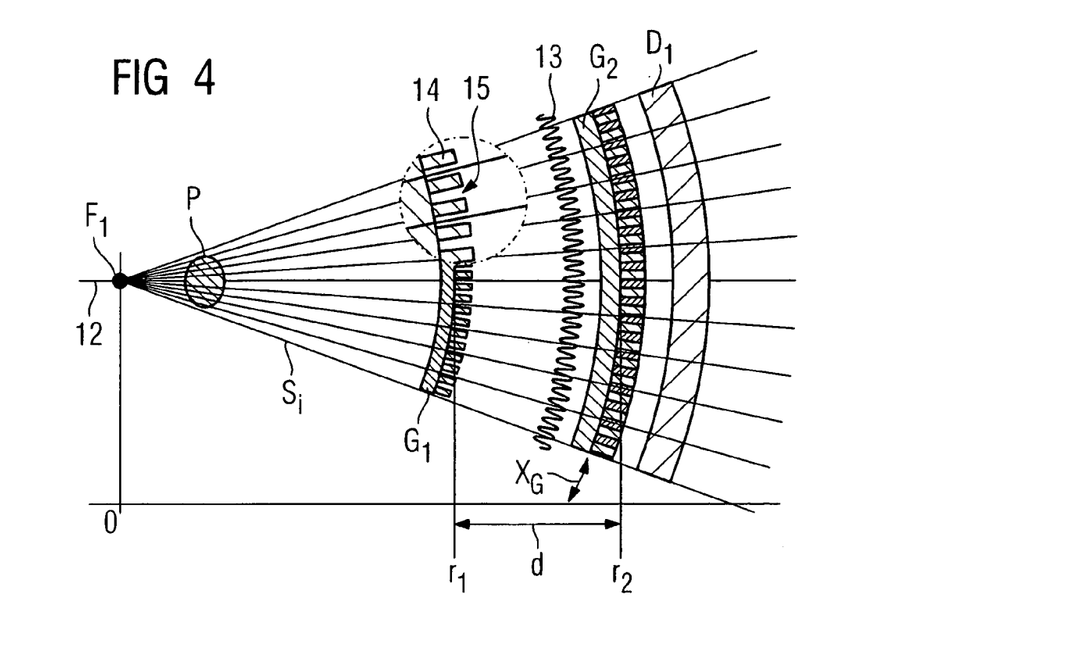
FIG. 4: shows a longitudinal section through a focus-detector system with a point-like focus, a concentrically curved phase grating and an analyzer grating, including concentrically curved detector surface.

In order to avoid this problem, an embodiment of the invention now proposes that at least one grating be configured so that it includes bars which are free from overhangs forming shadows in the beam path of the fan-shaped or conical beam of rays. This may for example be achieved by the two fundamentally different alternative embodiments described below, and optionally combinations of these variants:

Curved Gratings:

One alternative embodiment according to an embodiment of the invention proposes an X-ray optical system consisting of a point-like focus $F_1$, curved gratings $G_1$ and $G_2$ with a radial orientation of the bars 14 and a curved detector $D_1$, as represented by way of example in FIG. 4. The center of the curvature of the gratings $G_1$ and $G_2$ is positioned here on the optical axis 12 at the focal point of the radiation source, here the focus $F_1$, i.e. the radii of curvature $r_1$ and $r_2$ are respectively equal to the distance between the radiation source and the respective grating $G_1$ and $G_2$. In this X-ray optical system, both the phase grating $G_1$ acting as a beam splitter and the amplitude grating $G_2$ acting as an analyzer are thus curved and centered on the same focal point. The gratings $G_1$ and $G_2$ may be curved in one or two planes. With this X-ray optical system comprising curved gratings, it is possible to avoid the shadow effect which otherwise occurs with known flat gratings in conjunction with large cone angles. The gratings are curved so that the center of the grating, which is curved over a circular cylinder or a sphere surface, lies at the focus of the radiation source.

It should be pointed out that an optionally provided source grating may also have a correspondingly curved surface and bars aligned in the beam direction according to the embodiment of a focus-detector system in FIG. 3.

In order to produce a standing wave field in a cone beam or fan beam geometry, the following relationship must apply between the diffraction angle $2\Theta$ of first order reflections and the cone angle of the phase grating period $\Delta\alpha$:

$2\Theta > \Delta\alpha/2$, where $\Theta = \arcsin(\lambda/2g_1)$ and $\alpha = \arc(g_1/r_1)$, $g_1$ corresponds to the period of the phase grating $G_1$ and $r_1$ corresponds to the radius of curvature of the grating $G_1$, which is equal to the source-phase grating $G_1$ distance. For a wavelength $\lambda$, which is required in order to achieve penetration through the subject in radiography, the period $g_1$ of the phase grating $G_1$ is generally of the order of several µm, although it could also be smaller or larger depending on the source-phase grating $G_1$ distance.

In principle any grating with the requisite periodicity may be used as a beam splitter, although using phase gratings with a phase change of $\pi$ has the advantage that a high proportion of the incident intensity is diffracted. In order to obtain a phase change of $\pi$ for the resonant energy E corresponding to the wavelength $\lambda$, i.e. in order to obtain a maximal intensity in diffraction orders +1 and −1, the height $h_1$ of the phase grating $G_1$ is described with the aid of the following formula:

$$h = \frac{\lambda}{2\delta},$$

where $\delta$ is the real decrement of the refractive index of the grating material.

For low photon energies, bars made of materials with a low atomic number are proposed for the gratings, for example aluminum, silicon, diamond or plastic. For high photon energies, bars made of materials with a higher atomic number are proposed, for example chromium, nickel, molybdenum, tantalum, tungsten, platinum, gold, lead, uranium or compositions comprising these elements. With the latter materials, the requisite phase change of $\pi$ can be achieved with lower bar heights which can be produced more easily and which do not collimate the rays too much.

In order to avoid unnecessary intensity losses, a carrier material/wafer with as small as possible a mass absorption coefficient may be selected, for example a silicon wafer or a plastic carrier.

The grating should have a gap to bar width ratio of 1:1, in order to obtain the highest intensity of diffraction orders +1 and −1; different ratios favor other diffraction orders.

The profile of the grating is generally rectangular, although other profiles also function and influence the distribution of the intensities over the various diffraction orders. With a rectangular grating profile, the intensity of diffraction orders +1 and −1 is approximately 85% of the primary beam. Using a sinusoidal grating profile, apart from negligible absorption losses, the intensity of diffraction orders +1 and −1 approaches 100%.

In the parallel beam geometry, the transverse period of the standing wave field is half the period of the phase grating:

$$g_2 = \frac{1}{2} g_1.$$

Standing waves are formed along the optical axis, which is well known as the Talbot effect. The shortest distance $d_1$ where the contrast of the interfering fringes i.e. the standing wave field exhibits a maximum, the so-called $1^{st}$ Talbot distance, depends on the wavelength and the grating period $g_1$ and can be approximated as follows:

$$d_1 = \frac{1}{2} \frac{g_1^2}{4\lambda}.$$

In the cone or fan beam geometry, the transverse period of the transverse standing waves also depends on the distance from the source. To first approximation this may be regarded as a magnifying projection geometry, where the transverse period of the standing wave field at the first Talbot distance $d_1$ is:

$$g_2 = \frac{1}{2} \cdot \frac{r_2}{r_1} \cdot g_1.$$

The modulation and phase of this standing wave field is influenced by the phase shifts introduced by the phase object. In principle, a detector with sufficient resolution would be capable of registering the characteristics of the standing wave field and thereby make it possible to image the object. For this, its resolution must be of the order of the period of the standing wave field or better. Such variants are proposed in patent applications DE 10 2006 017 290 and DE 10 2006 017 291.4 (the entire contents of each of which is hereby incorporated herein by reference), and may also be used here. If such detectors are not available, an analyzer grating with sufficient resolution may be inserted at the position of the standing wave field, preferably at the first Talbot distance. By scanning this analyzer grating along the standing waves of the same Talbot order, it is possible to determine the phase, amplitude and offset of the sinusoidal intensity profile.

For this procedure, it is necessary to record at least three measurement points at which the grating is shifted by fractions of the period $g_2$, preferably with a spacing of $g_2/3$. In practice, this scan is carried out in four or more steps with an increment of $g_2/4$ or less. For this scan, in the ideal case a rotational movement about the source must be carried out. The short scan length, however, also permits a linear scan transversely to the optical axis.

In this alternative embodiment it is proposed that the analyzer grating $G_2$, also referred to as an amplitude grating, be embodied as a curved grating with radial orientation of the bars. The normals to the surface of the curved gratings should intersect the optical axis at the focus of the source, i.e. the radius of curvature is equal to the distance $r_2$ between the source and the grating. The grating in the one-dimensional case therefore has the configuration of a circular cylinder section and in the two-dimensional case the configuration of a spherical cap, the axis of the cylinder or the center of the sphere lying at the source point or focus of the X-ray source. The amplitude grating, which acts as an analyzer, may likewise be centered on the source. The analyzer grating may be curved in one or two planes according to the configuration of the phase grating $G_1$. Owing to the curved configuration of the grating, the bars are aligned radially and the shadowing effect, which would apply for flat gratings at high cone angles, can be avoided.

The detector, for example a CCD, is placed directly behind the analyzer grating. The pixel resolution of the detector determines the position resolution, with which the object is imaged. When using an analyzer grating, however, in contrast to the propagation method, it is not necessary to resolve the interference fringes with the detector itself. This is done here by the fine-resolving analyzer grating. The magnification effect may furthermore be utilized in the cone or fan geometry, so that an object is imaged with high position resolution by a detector of a lower position resolution.

So that the phase grating acts as a diffraction grating or beam splitter and an interference pattern can be created behind the phase grating, the incident X-radiation must satisfy coherence requirements at the phase grating. Coherent illumination of at least two neighboring bars of the phase grating must be provided. This means that the transverse coherence length must be at least of the order of the grating period $g_1$. Besides the observation distance and the wavelength, the coherence length is also determined by the source size, in particular the transverse dimensions of the focus.

Figure 6:
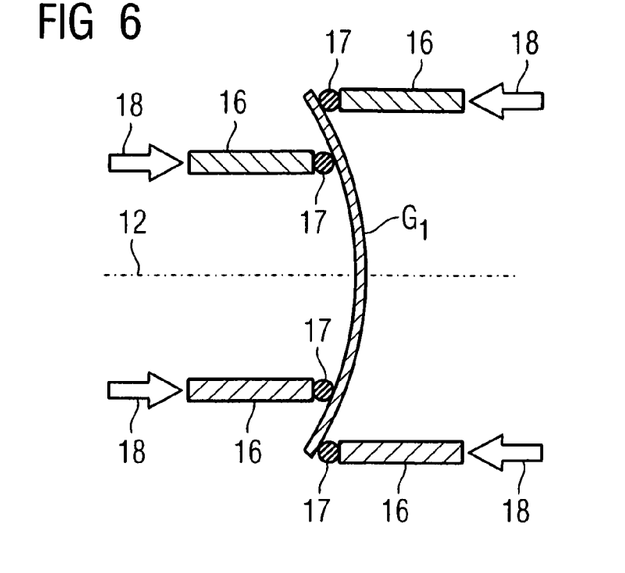
FIG. 6: shows an embodiment of a grating curved by four support elements.
Figure 7:
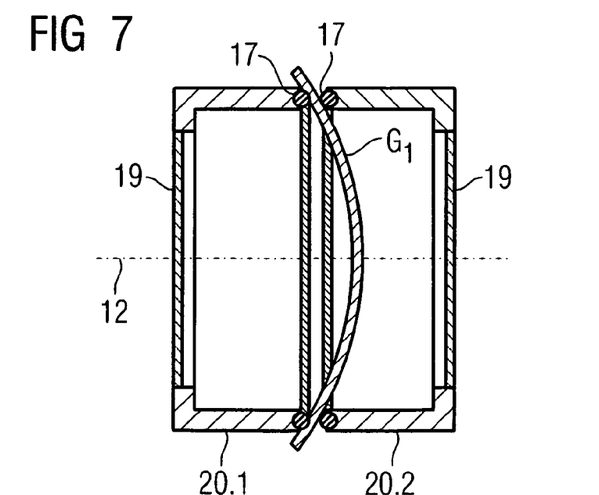
FIG. 7: shows an embodiment of a grating curved by pressure chambers arranged on either side with different pressurization.

For a circular 1D curvature of the gratings, two techniques are proposed by way of example which are represented in FIGS. 6 and 7:

(i) FIG. 6 shows a rectangular grating $G_1$ with a substrate/wafer of homogeneous thickness, apart from the bars, which is curved with the aid of four support elements 16 on four bearing lines—4 bearing points are represented in the cross-sectional drawing of FIG. 6—by offset and counteracting forces 18. Owing to the symmetrical loads, the part of the grating/wafer between the two bearing lines is free of external forces and is exposed only to a constant moment. A constant radius of curvature is therefore obtained, i.e. a 1-dimensional circular cylindrically curved grating.

(ii) FIG. 7 shows another embodiment, in which the rectangular grating $G_1$ or the wafer is positioned leaktightly by seals 17 on a pressure or vacuum chamber, rectangular in cross section, with the two chamber halves 20.1 and 20.2 and the windows 19. Two opposite edges are configured to be straight and mutually parallel. The other edges have the desired circular profile. By exerting pressure differences on the two sides of the grating $G_1$, the grating is pressed into the desired circularly curved configuration. A one-dimensionally curved grating is obtained in the form of a circular cylinder section. In order to ensure a homogeneous curvature of the grating in spite of the anisotropic flexibility of the grating material, the grating bars and the principal crystallographic axes of the substrate (the [100] and [010] orientations in silicon) should be aligned parallel to the pressure chamber, or the bearing lines. In order to avoid edge effects, in both flexural arrangements the dimension of the grating perpendicular to the plane of the drawing should be sufficiently large in comparison with the circular extent of the grating.

In order to spherically curve a grating two-dimensionally, the grating is positioned on a circular pressure or vacuum chamber. The grating is to be sealed in a leaktight fashion on the circular frame, i.e. the chamber edges. By exerting pressure differences on the two sides of the grating, the grating is pressed into the desired configuration, two-dimensionally curved circularly, i.e. in the form of a spherical cap.

For applications in radiology, the detector need not necessarily be curved. A flat detector also fulfils these functions. For an application in CT, however, a detector with a curved profile is preferred.

It should furthermore be pointed out that besides gases, in principle it is also possible to use liquids as a pressure-generating medium. Likewise, for example, it is also possible to use only one of the chamber halves 20.2 if a negative pressure is set up there relative to the prevailing atmospheric pressure.

Figure 5:
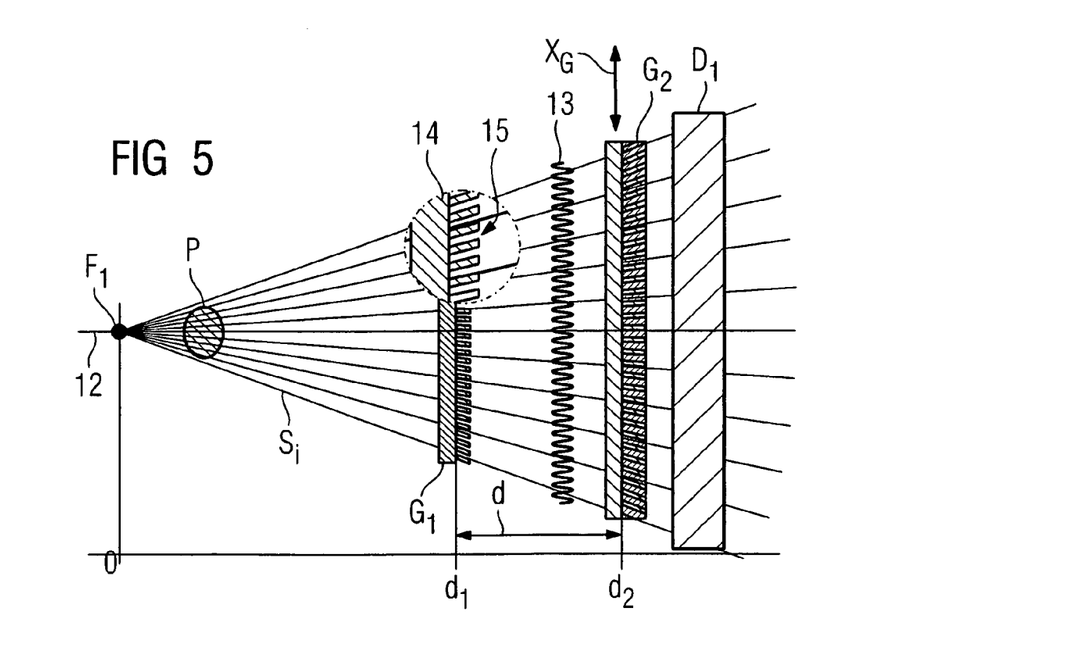
FIG. 5: shows a longitudinal section through a focus-detector system with a point-like focus, a flat phase grating, an analyzer grating and a detector, but radial alignment of the grating bars.

Flat Gratings with Inclined Bars:

Another alternative embodiment also proposes an X-ray optical system with flat gratings $G_1$ and $G_2$, but with radially aligned structuring as shown in FIG. 5. The center of the grating orientation is positioned here on the optical axis at the focal point of the source $F_1$. The gratings $G_1$ and $G_2$ are positioned symmetrically with respect to the optical axis, the bars and gaps being aligned with the line focus or point focus of the X-ray source. In this X-ray optical system the phase grating $G_1$, which acts as a beam splitter, and the amplitude grating $G_2$, which acts as an analyzer, are oriented toward the same focal point $F_1$ in respect of the alignment of the bars 14. In this way, it is possible to produce both 1D and 2D grating structures and with this X-ray optical system, via grating bars and gaps oriented in an inclined fashion, it is possible to avoid the shadowing effect which would occur with flat gratings at higher cone angles.

The dimensions of this embodiment with flat gratings follow the principles outlined above for curved gratings. The deviation from curved gratings to flat gratings with inclined bars, however, represents a departure from strict theory. For beam paths with a moderate cone angle, this embodiment nevertheless offers technical advantages.

The aforementioned grating has the advantage that means for bringing it into a well-defined circular configuration can be obviated, or at least it is possible to work with a smaller curvature.

The inclined orientation of gaps and bars in the grating may, for example, be achieved by the following two etching processes.

(i) In plasma or dry etching processes, by inclining the wafer with respect to the electric field of the plasma.

(ii) In wet chemical etching, by photo-controlled etching attack. To this end, starting defects are etched in a first step at lithographically defined structure patterns on the wafer front side by means of a KOH etchant. In a second step, an HF etchant is used on the wafer front side and the wafer is simultaneously exposed to IR light from the rear side. This utilizes the fact that the etching attack in lightly n-doped silicon is controlled by the electrical holes (defect electrons). The generation of electrical holes in n-doped silicon can be controlled by the incident IR light (IR—infrared).

Since the silicon is transparent to IR, the illumination can be carried out from the rear side of the wafer. The illumination direction and the starting defects, pre-etched with KOH, control the direction and configuration of the etched pores or gaps.

Owing to the inclination of the bars, the bar lengths in the beam direction are not equal but differ according to the distance from the optical axis, even though the bar height (perpendicular height from the grating surface) is the same. The effect of this is that the grating provides a phase shift of exactly $\pi$ for a particular wavelength only in a few small areas. With an optimized design, the etching of the gaps should therefore be controlled so that the bar lengths in the beam direction are homogeneous over the entire wafer. The aforementioned photoassisted etching process provides this opportunity. When using other etching processes which do not offer this control option, a possible alternative would be a subsequent polishing process by which the height of the bars can be adjusted.

Owing to the fan-like or conical beam geometry, for a constant Talbot distance the X-ray standing wave field would be slightly curved even with bars of equal height. This slight discrepancy can be neglected to first order, when the typical sizes of the Talbot distances along the optical axis are taken into account. When considered in more detail, however, the variation of the grating periods with the distance from the optical axis according to the aforementioned equation for the Talbot distances provides an opportunity to align the standing wave field in a plane or adapt/adjust it to the actual distance of the analyzer grating or the analyzing detector.

In principle, three variants may thus be presented for adjusting the X-ray optical grating to the relevant geometrical premises:

The length of the bars of the grating may be varied, the curvature of the grating may be adjusted and the grating period may be varied. For clarification, it should be mentioned that in the case of perpendicular bars, the bar heights and the bar lengths are the same.

In order to obtain bars of variable length, a curved length profile may be used for the bars. In other words, in order to compensate for a variable distance to the analyzer grating, the bars may be varied in length according to requirements over the surface of the grating. For example, bars with a larger distance from the center of the grating may be given a smaller perpendicular height than bars at the center of the grating. The bar length—relative to the beam direction, i.e. the path of the ray through the bar—thus remains the same over the entire surface of the grating. In this way, all bars are adapted to the same wavelength of the X-radiation. Technologically, this can be achieved by a polishing process as is known in the optics industry, which is applied to the silicon wafer surface before etching the gaps. Nevertheless, the possibility of over- or undercompensating for the inclination of the bars also exists.

If a curved Talbot profile is created with a cone beam geometry: In order to avoid the need for a curved absorber profile, all Talbot distances may be adjusted in the same vertical plane, specifically the plane of the absorber grating. To this end, the grating period in the vertical plane may be varied continuously so that the resulting Talbot distances always and optimally correspond to the target plane, not only to first approximation. Since the Talbot distance depends on the grating period, this means that the grating period will be adjusted progressively as a function of the distance from the optical axis.

In this way, even small areas of the interferometer can be tuned to different wavelengths of the X-radiation. In order to handle this approach involving variable Talbot distances when there is a uniform grating period, the Inventors propose that the phase grating be tuned locally for different wavelengths. The object is therefore that the fringes of maximal amplitude always occur in the same plane. Since the Talbot distance depends on the wavelength, this means that the phase grating will be tuned for different wavelengths according to the distance from the optical axis. The bars consequently have different lengths, in order to resonate for different wavelengths. This requires bars with a defined length profile, which can be achieved by polishing the grating surface as in the case of an optical lens (see above).

Figure 9:
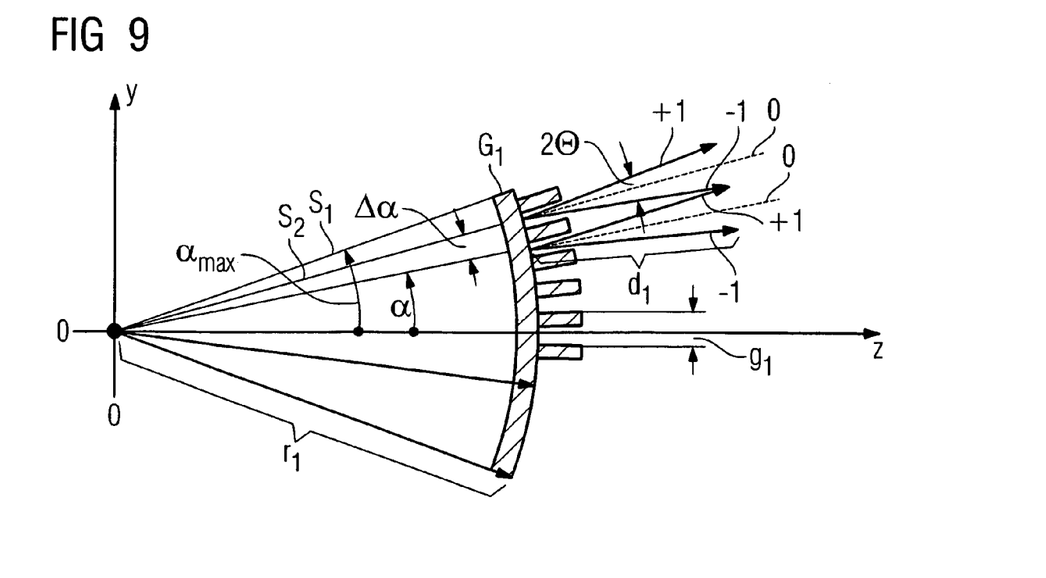
FIG. 9: shows a graphical representation of the diffraction of X-rays at the phase grating and representation of the Talbot distance.

A graphical representation of this problem is represented in FIG. 9, the individual rays being denoted by $S_i$ and the $+1^{st}$ and $-1^{st}$ order diffraction at the first Talbot distance $d_1$ being shown behind the phase grating $G_1$. The following geometrical relationship should be satisfied here $2\Theta > \Delta\alpha/2$, $\Theta$ describing half the first order diffraction angle of the relevant X-rays $S_i$ at the diffraction grating with $\Theta = \arcsin(\lambda/2g_1)$, $\Delta\alpha$ describing the cone angle of the phase grating period according to $\Delta\alpha = \arc(g_1/r_1)$, $g_1$ describing the period of the phase grating $G_1$, $r_1$ describing the radial distance from the focus to the phase grating and $\lambda$ describing the wavelength of the energy of the X-rays in question.

It is now advantageous that imaging with curved gratings, or grating bars oriented so that they are inclined, in phase contrast radiography and tomography benefits from an enlarged usable field of view. This gives a better dose efficiency, and fast diagnoses and analyses are made possible.

In micro-radiography and tomography, the described grating system makes it possible for the object to be positioned not only directly before or after the phase grating but also close to the source. This permits a magnifying geometry which, especially in the case of nondestructive testing, allows small objects to be magnified under the conditions of differential phase contrast imaging. This obviates the need to adapt the detector resolution to the optically desired resolution. Instead, the magnification of the projection geometry reduces the required detector resolution by the magnification factor.

This example description relates substantially to the phase grating, although the considerations for configuration and dimensioning may in principle also be applied to the analyzer grating and the source grating. The period of the analyzer grating is given—as described—directly by the period of the phase grating. There is no critical tuning of the depth of the gaps (thickness of the absorber) in the sense of tuning to a resonant energy, although the absorber must be sufficiently thick, more than three times the absorption length and preferably even thicker. A material with as high as possible a mass absorption coefficient for the desired resonant energy should furthermore be selected (for example: Ta, W, Pt, Au, Pb, U). Depending on the dimensioning of the phase grating —as described—various dimensioning rules are obtained for the shape of the analyzer grating. In order to avoid unnecessary intensity losses, a carrier material with as low as possible a mass absorption coefficient should be selected.

A shadow-free configuration is advantageous for the source grating as well. An embodiment as a curved grating or a grating with inclined bars is likewise possible. In this context, it is in principle also possible to use a source with a strip anode, i.e. an anode with a grating-like design of the X-radiation emission sites. The period is given by the described lever ratio. The ratio of the width of the grating gaps to the width of the grating bars may advantageously lie between 1:10 and 1:1. The number of grating gaps may favorably lie in the range of from 1 to approximately 20. There is no critical tuning of the depth of the gaps (thickness of the absorber) in the sense of tuning to a resonant energy, although the absorber must be sufficiently thick, i.e. the thickness of the absorber should be more than three times the absorption length. A material with as high as possible a mass absorption coefficient for the desired resonant energy should furthermore be selected (for example: Ta, W, Pt, Au, Pb, U). In order to avoid unnecessary intensity losses, the carrier material should be thin and a carrier material with as low as possible a mass absorption coefficient should be selected.

Figure 8:
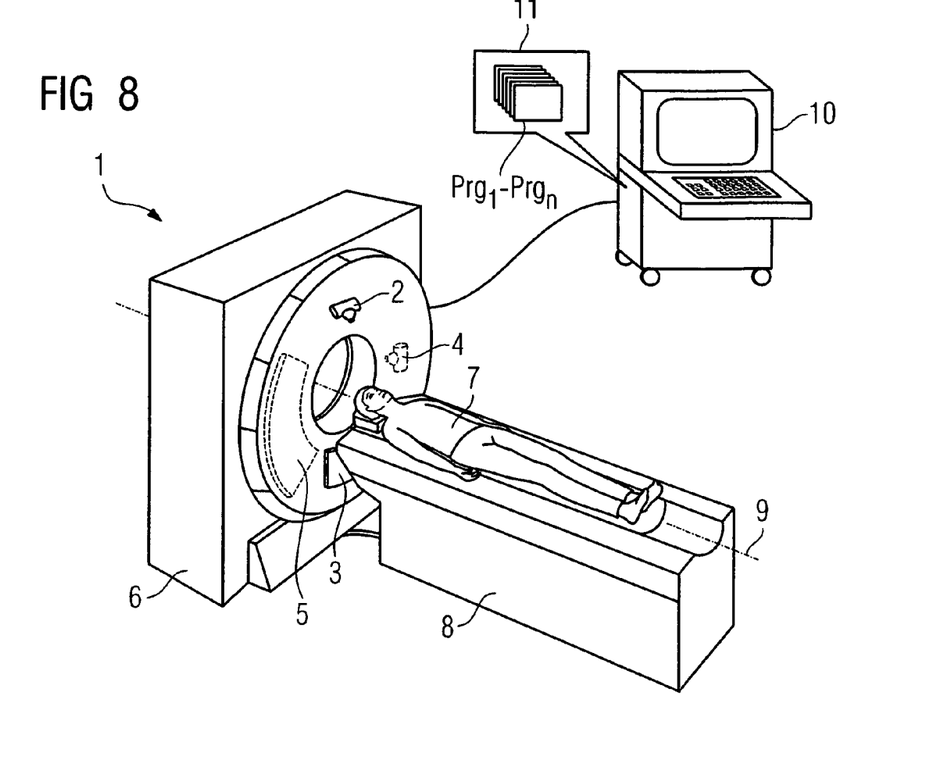
FIG. 8: shows a medical X-ray CT system in 3D view with a focus-detector system according to the invention.

FIG. 8 represents a complete computer CT system with focus-detector systems according to the invention for carrying out the method according to the invention, by way of example and also generically for other X-ray systems, in particular X-ray systems for generating projective phase contrast recordings and for C-arc equipment. This figure shows the CT system 1 which includes a first focus-detector system with an X-ray tube 2 and a detector 3 lying opposite, which is arranged on a gantry (not represented in detail) in a gantry housing 6. A grating system according to FIGS. 1 to 3 is arranged in the beam path of the first focus-detector system 2, 3 so that the patient 7, who lies on a patient support 8 displaceable along the system axis 9, can be displaced into the beam path of the first focus-detector system and scanned there. The CT system is controlled by a computation and control unit 10 in which programs $Prg_1$ to $Prg_n$ are stored in a memory 11, which carry out the method according to an embodiment of the invention as described above and reconstruct corresponding tomographic images from the measured ray-dependent phase shifts and absorptions.

Instead of a single focus-detector system, a second focus-detector system may optionally be arranged in the gantry housing. This is indicated in FIG. 8 by the X-ray tube 4 shown in dashes and the detector 5 represented in dashes.

At least in one focus-detector system, there is a grating according to an embodiment of the invention in which the grating structure, which is needed for the detection of phase contrast recordings, is generated in the grating medium by a standing ultrasound wave.

In another configuration of the focus-detector system, gratings may also be formed by a grating medium in which a grating structure for the X-radiation is formed with the aid of an ultrasound standing wave field.

Moreover, it should also be pointed out that the focus-detector systems as presented are not only capable of measuring phase shifts of the X-radiation, rather they are furthermore suitable for conventional measurement of the radiation absorption and reconstruction of corresponding absorption recordings. Optionally, combined absorption and phase contrast recordings may even be generated.

It is to be understood that the features of the invention as mentioned above may be used not only in the combination respectively indicated, but also in other combinations or in isolation, without departing from the scope of the present invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A focus-detector arrangement of an X-ray apparatus for generating at least one of projective and tomographic phase contrast recordings of a subject, comprising:

a radiation source with a focus, arranged on a first side of the subject, to generate a fan-shaped or conical beam of X-rays;

at least one X-ray optical grating arranged in the beam path, with at least one phase grating arranged on an opposite second side of the subject in the beam path to generate an interference pattern of the X-radiation; and an analysis-detector system to detect at least the interference pattern generated by the phase grating in respect of its phase shift with position resolution, wherein the at least one X-ray optical grating comprises bars which are free from overhangs forming shadows in the beam path of the fan-shaped or conical beam of rays, wherein the at least one X-ray optical grating is designed to be curved around the focus at least in a first section plane.

2. The focus-detector arrangement as claimed in claim 1, wherein the at least one X-ray optical grating has a radius of curvature around the focus in the first section plane.

3. The focus-detector arrangement as claimed in claim 1, wherein the at least one X-ray optical grating is designed to be curved around the focus in a second section plane perpendicular to the first section plane.

4. The focus-detector arrangement as claimed in claim 3, wherein the at least one X-ray optical grating has a radius of curvature around the focus in the second section plane.

5. The focus-detector arrangement as claimed in claim 1, wherein the curvature of the at least one X-ray optical grating in a plane is induced by clamping between at least three support elements.

6. The focus-detector arrangement as claimed in claim 5, wherein at least one of the support elements bears pointwise on the at least one X-ray optical grating.

7. The focus-detector arrangement as claimed in claim 5, wherein at least one of the support elements bears linearly on the at least one X-ray optical grating.

8. The focus-detector arrangement as claimed in claim 1, wherein the at least one X-ray optical grating constitutes a bounding surface between at least two regions of different gas pressure and a desired curvature of the at least one X-ray optical grating in the at least one first section plane is induced by a pressure difference between the regions of different gas pressure.

9. The focus-detector arrangement as claimed in claim 1, wherein the following geometrical condition is satisfied at least for the average value of the radial distances from the focus ($F_1$) to the at least one phase grating ($G_1$) and from the focus ($F_1$) to the analysis-detector system ($G_2$, $D_1$):

$$g_2 = \frac{1}{2} \cdot \frac{r_2}{r_1} \cdot g_1,$$

where:
$r_1$=radial distance from the focus to the at least one phase grating;
$r_2$=radial distance from the focus to the analysis-detector system;
$g_1$=period of the at least one phase grating ($G_1$);
$g_2$=period of the analysis-detector system.

10. The focus-detector arrangement as claimed in claim 1, wherein the following geometrical condition is satisfied:

$$r_1 > \frac{g_1^2}{2\lambda},$$

where:
$r_1$=radial distance from the focus to the at least one phase grating;
$g_1$=period of the at least one phase grating ($G_1$);
$\lambda$=wavelength of the energy of the X-radiation in question.

11. The focus-detector arrangement as claimed in claim 1, wherein the following geometrical condition is satisfied:

$$r_2 - r_1 = d = \frac{1}{2} \cdot \frac{g_1^2}{4 \cdot \lambda},$$

where:
$r_1$=radial distance from the focus to the at least one phase grating;
$r_2$=radial distance from the focus to the analysis-detector system;
$g_1$=period of the at least one phase grating ($G_1$);
d=distance from the at least one phase grating to the analysis-detector system;
$\lambda$=wavelength of the energy of the X-radiation in question.

12. The focus-detector arrangement as claimed in claim 1, wherein the following geometrical condition is satisfied:

$2\Theta > \Delta\alpha/2$, where:
$\Theta$=half the first order diffraction angle of the X-radiation in question on the at least one phase grating with $\Theta$=arcsin($\lambda/2g_1$);
$\Delta\alpha$=cone angle of the at least one phase grating according to $\Delta\alpha$=arc($g_1/r_1$);
$g_1$=period of the at least one phase grating ($G_1$);
$r_1$=radial distance from the focus to the at least one phase grating;
$\lambda$=wavelength of the energy of the X-radiation in question.

13. The focus-detector arrangement as claimed in claim 1, wherein the focus is substantially designed to be point-like.

14. The focus-detector arrangement as claimed in claim 1, wherein a source grating for generating a beam of quasi-coherent rays is arranged between the focus and the subject.

15. The focus-detector arrangement as claimed in claim 1, wherein the analysis-detector system is designed as a combination of a single- or multiline detector having a multiplicity of detector elements, which determine the resolution of the system, and an analyzer grating upstream in the radiation direction for position-resolved determination of the average phase shift of the X-radiation of a particular energy per detector element.

16. The focus-detector arrangement as claimed in claim 15, wherein the detector of the analysis-detector system has a curvature around the focus.

17. The focus-detector arrangement as claimed in claim 16, wherein the analyzer grating of the analysis-detector system has a curvature around the focus.

18. The focus-detector arrangement as claimed in claim 15, wherein the analyzer grating of the analysis-detector system has a curvature around the focus.

19. The focus-detector arrangement as claimed in claim 1, wherein the detector of the analysis-detector system has a curvature around the focus.

20. The focus-detector arrangement as claimed in claim 1, wherein the distance from the focus to the subject is designed so that it is small (½x-⅒x) to very small (<⅒x) relative to the distance from the subject to the analysis-detector system.

21. An X-ray system for generating projective phase contrast recordings, comprising a focus-detector arrangement as claimed in claim 1.

22. An X-ray C-arc system for generating projective or tomographic phase contrast recordings, comprising a focus-detector arrangement as claimed in claim 1.

23. An X-ray CT system for generating tomographic phase contrast recordings, comprising a focus-detector arrangement as claimed in claim 1.

24. A focus-detector arrangement of an X-ray apparatus for generating at least one of projective and tomographic phase contrast recordings of a subject, comprising:
a radiation source with a focus, arranged on a first side of the subject, to generate a fan-shaped or conical beam of X-rays;
at least one X-ray optical grating arranged in the beam path, with at least one phase grating arranged on an opposite second side of the subject in the beam path to generate an interference pattern of the X-radiation; and
an analysis-detector system to detect at least the interference pattern generated by the phase grating in respect of its phase shift with position resolution, wherein the at least one X-ray optical grating comprises bars which are free from overhangs forming shadows in the beam path of the fan-shaped or conical beam of rays, wherein the at least one X-ray optical grating is designed to be curved around the focus at least in a first section plane, wherein the bars of the at least one X-ray optical grating exclusively comprise rising and falling flanks which are aligned radially toward the focus.

25. The focus-detector arrangement as claimed in claim 24, wherein each bar of the at least one X-ray optical grating comprises a plateau which is arranged perpendicularly to that X-ray of the beam of X-rays which passes through.

26. The focus-detector arrangement as claimed in claim 24, wherein the at least one X-ray optical grating is designed to be flat overall.

27. The focus-detector arrangement as claimed in claim 26, wherein the bars of the at least one X-ray optical grating are aligned radially toward the focus in at least one section plane.

28. The focus-detector arrangement as claimed in claim 27, wherein the bars of the at least one X-ray optical grating are three-dimensionally aligned radially toward the focus.

29. The focus-detector arrangement as claimed in claim 24, wherein the bars of the at least one X-ray optical grating have an at least substantially sinusoidal height profile in at least one first section plane along the beam path.

30. The focus-detector arrangement as claimed in claim 29, wherein the bars of the at least one X-ray optical grating have at least one of a sinusoidal, curvilinear and trapezoidal height profile in two mutually perpendicular section planes along the beam path.

31. The focus-detector arrangement as claimed in claim 24, wherein the following geometrical condition is satisfied at least for the average value of the radial distances from the focus ($F_1$) to the at least one phase grating ($G_1$) and from the focus ($F_1$) to the analysis-detector system ($G_2$, $D_1$):

$$g_2 = \frac{1}{2} \cdot \frac{r_2}{r_1} \cdot g_1,$$

where:
$r_1$=radial distance from the focus to the at least one phase grating;
$r_2$=radial distance from the focus to the analysis-detector system;
$g_1$=period of the at least one phase grating ($G_1$);
$g_2$=period of the analysis-detector system.

32. The focus-detector arrangement as claimed in claim 24, wherein the following geometrical condition is satisfied:

$$r_1 > \frac{g_1^2}{2\lambda},$$

where:
$r_1$=radial distance from the focus to the at least one phase grating;
$g_1$=period of the at least one phase grating ($G_1$);
$\lambda$=wavelength of the energy of the X-radiation in question.

33. The focus-detector arrangement as claimed in claim 24, wherein the following geometrical condition is satisfied:

$$r_2 - r_1 = d = \frac{1}{2} \cdot \frac{g_1^2}{4 \cdot \lambda},$$

where:
$r_1$=radial distance from the focus to the at least one phase grating;
$r_2$=radial distance from the focus to the analysis-detector system;
$g_1$=period of the at least one phase grating ($G_1$);
d=distance from the at least one phase grating to the analysis-detector system;
$\lambda$=wavelength of the energy of the X-radiation in question.

34. The focus-detector arrangement as claimed in claim 24, wherein the following geometrical condition is satisfied:

2Θ>Δα/2, where:
Θ=half the first order diffraction angle of the X-radiation in question on the at least one phase grating with Θ=arcsin ($\lambda/2g_1$);
Δα=cone angle of the at least one phase grating according to Δα=arc($g_1/r_1$);
$g_1$=period of the at least one phase grating ($G_1$);
$r_1$=radial distance from the focus to the at least one phase grating;
$\lambda$=wavelength of the energy of the X-radiation in question.

35. The focus-detector arrangement as claimed in claim 24, wherein the focus is substantially designed to be point-like.

36. The focus-detector arrangement as claimed in claim 24, wherein a source grating for generating a beam of quasi-coherent rays is arranged between the focus and the subject.

37. The focus-detector arrangement as claimed in claim 24, wherein the analysis-detector system is designed as a combination of a single- or multiline detector having a multiplicity of detector elements, which determine the resolution of the system, and an analyzer grating upstream in the radiation direction for position-resolved determination of the average phase shift of the X-radiation of a particular energy per detector element.

38. The focus-detector arrangement as claimed in claim 37, wherein the detector of the analysis-detector system has a curvature around the focus.

39. The focus-detector arrangement as claimed in claim 38, wherein the analyzer grating of the analysis-detector system has a curvature around the focus.

40. The focus-detector arrangement as claimed in claim 37, wherein the analyzer grating of the analysis-detector system has a curvature around the focus.

41. The focus-detector arrangement as claimed in claim 24, wherein the detector of the analysis-detector system has a curvature around the focus.

42. The focus-detector arrangement as claimed in claim 24, wherein the distance from the focus to the subject is designed so that it is small ($\frac{1}{2}$x-$\frac{1}{10}$x) to very small (<$\frac{1}{10}$x) relative to the distance from the subject to the analysis-detector system.

43. An X-ray system for generating projective phase contrast recordings, comprising a focus-detector arrangement as claimed in claim 24.

44. An X-ray C-arc system for generating projective or tomographic phase contrast recordings, comprising a focus-detector arrangement as claimed in claim 24.

45. An X-ray CT system for generating tomographic phase contrast recordings, comprising a focus-detector arrangement as claimed in claim 24.

46. A focus-detector arrangement of an X-ray apparatus for generating at least one of projective and tomographic phase contrast recordings of a subject, comprising:
  a radiation source with a focus, arranged on a first side of the subject, to generate a fan-shaped or conical beam of X-rays;
  at least one X-ray optical grating arranged in the beam path, with at least one phase grating arranged on an opposite second side of the subject in the beam path to generate an interference pattern of the X-radiation; and
  an analysis-detector system to detect at least the interference pattern generated by the phase grating in respect of its phase shift with position resolution, wherein the at least one X-ray optical grating comprises bars which are free from overhangs forming shadows in the beam path of the fan-shaped or conical beam of rays wherein there is a different distance from the at least one X-ray optical grating to the analysis-detector system over the extent of the at least one X-ray optical grating.

47. The focus-detector arrangement as claimed in claim 46, wherein bars of the at least one phase grating comprise different bar lengths in order to adapt a Talbot distance to a different distance from the analysis-detector system.

48. The focus-detector arrangement as claimed in claim 46, wherein bars of the at least one phase grating comprise different grating periods in order to adapt a Talbot distance to a different distance from the analysis-detector system.

49. A focus-detector arrangement of an X-ray apparatus for generating at least one of projective and tomographic phase contrast recordings of a subject, comprising:
  a radiation source with a focus, arranged on a first side of the subject, to generate a fan-shaped or conical beam of X-rays;
  at least one X-ray optical grating arranged in the beam path, with at least one phase grating arranged on an opposite second side of the subject in the beam path to generate an interference pattern of the X-radiation; and
  an analysis-detector system to detect at least the interference pattern generated by the phase grating in respect of its phase shift with position resolution, wherein the at least one X-ray optical grating comprises bars which are free from overhangs forming shadows in the beam path of the fan-shaped or conical beam of rays, wherein the at least one X-ray optical grating is designed to be curved around the focus at least in a first section plane wherein the distance from the at least one phase grating to the analysis-detector system is the same over the extent of the at least one phase grating.

50. The focus-detector arrangement as claimed in claim 49, wherein bars of the at least one phase grating comprise the same bar lengths with a different bar height in order to adapt a Talbot distance to the same distance from the analysis-detector system.

51. The focus-detector arrangement as claimed in claim 49, wherein bars of the at least one phase grating comprise different grating periods with the same bar height and different bar length in order to adapt a Talbot distance to the same distance from the analysis-detector system.

52. A focus-detector arrangement of an X-ray apparatus for generating at least one of projective and tomographic phase contrast recordings of a subject, comprising:
  a radiation source with a focus, arranged on a first side of the subject, to generate a fan-shaped or conical beam of X-rays;
  at least one X-ray optical grating arranged in the beam path, with at least one phase grating arranged on an opposite second side of the subject in the beam path to generate an interference pattern of the X-radiation; and
  an analysis-detector system to detect at least the interference pattern generated by the phase grating in respect of its phase shift with position resolution, wherein the at least one X-ray optical grating comprises bars which are free from overhangs forming shadows in the beam path of the fan-shaped or conical beam of rays, wherein a curvature of the at least one X-ray optical grating in a plane is induced by clamping between at least three support elements.

53. A focus-detector arrangement of an X-ray apparatus for generating at least one of projective and tomographic phase contrast recordings of a subject, comprising:
  a radiation source with a focus, arranged on a first side of the subject, to generate a fan-shaped or conical beam of X-rays;
  at least one X-ray optical grating arranged in the beam path, with at least one phase grating arranged on an opposite second side of the subject in the beam path to generate an interference pattern of the X-radiation; and
  an analysis-detector system to detect at least the interference pattern generated by the phase grating in respect of its phase shift with position resolution, wherein the at least one X-ray optical grating comprises bars which are free from overhangs forming shadows in the beam path of the fan-shaped or conical beam of rays, wherein the at least one X-ray optical grating constitutes a bounding surface between at least two regions of different gas pressure and a desired curvature of the at least one X-ray optical grating in at least one first section plane is induced by a pressure difference between the regions of different gas pressure.

* * * * *